US010561549B2

(12) United States Patent
Walton et al.

(10) Patent No.: US 10,561,549 B2
(45) Date of Patent: Feb. 18, 2020

(54) BED-BASED SAFETY PROTOCOL CONTROL

(71) Applicant: Hill-Rom Services, Inc., Batesville, IN (US)

(72) Inventors: Kelly F. Walton, Cary, NC (US); Jennifer A. Gunn, Durham, NC (US); Kiana M. Dezelon, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 16/034,501

(22) Filed: Jul. 13, 2018

(65) Prior Publication Data

US 2019/0029900 A1    Jan. 31, 2019

Related U.S. Application Data

(60) Provisional application No. 62/538,090, filed on Jul. 28, 2017.

(51) Int. Cl.
| | |
|---|---|
| *A61G 7/018* | (2006.01) |
| *A61B 5/00* | (2006.01) |
| *A61G 13/12* | (2006.01) |
| *G16H 10/60* | (2018.01) |
| *G16H 40/63* | (2018.01) |
| *A61B 5/11* | (2006.01) |

(52) U.S. Cl.
CPC .............. *A61G 7/018* (2013.01); *A61B 5/447* (2013.01); *A61B 5/746* (2013.01); *A61G 13/1215* (2013.01); *G16H 10/60* (2018.01); *G16H 40/63* (2018.01); *A61B 5/002* (2013.01); *A61B 5/1115* (2013.01); *A61B 5/1117* (2013.01); *A61G 2203/16* (2013.01); *A61G 2203/20* (2013.01); *A61G 2203/44* (2013.01); *A61G 2205/50* (2013.01)

(58) Field of Classification Search
CPC combination set(s) only.
See application file for complete search history.

(56) References Cited

U.S. PATENT DOCUMENTS

| | | | |
|---|---|---|---|
| 5,561,412 | A | 10/1996 | Novak et al. |
| 5,715,548 | A | 2/1998 | Weismiller et al. |
| 7,296,312 | B2 | 11/2007 | Menkedick et al. |
| 7,319,386 | B2 | 1/2008 | Collins, Jr. et al. |

(Continued)

*Primary Examiner* — Nabil H Syed
*Assistant Examiner* — Cal J Eustaquio
(74) *Attorney, Agent, or Firm* — Barnes & Thornburg LLP

(57) ABSTRACT

A patient bed is provided in a healthcare facility having a network including a real time locating system (RTLS) and an electronic medical records (EMR) computer. The patient bed includes bed control circuitry that is configured to receive at least one protocol messages from the EMR computer and, in response to the at least one protocol message, enables at least one bed safety protocol in which at least one bed condition is monitored by the bed control circuitry. The bed control circuitry generates an alert in response to the at least one bed condition being in an undesirable state and no caregiver being present in the patient room as determined by the RTLS and communicated to the bed circuitry. The bed control circuitry suspends monitoring the at least one bed condition in response to the RTLS indicating to the bed control circuitry that at least one caregiver is present in the patient room.

22 Claims, 3 Drawing Sheets

(56) References Cited

U.S. PATENT DOCUMENTS

| | | |
|---|---|---|
| 7,443,302 B2 | 10/2008 | Reeder et al. |
| 7,538,659 B2 | 5/2009 | Ulrich et al. |
| 7,562,458 B1 * | 7/2009 | Clark, Jr. ............... A61G 7/018 |
| | | 33/333 |
| 7,679,520 B2 | 3/2010 | Zerhusen et al. |
| 7,771,386 B2 | 8/2010 | Eggers et al. |
| 7,911,349 B2 | 3/2011 | Zerhusen et al. |
| 8,046,625 B2 | 10/2011 | Ferguson et al. |
| 8,169,304 B2 | 5/2012 | Schuman, Sr. et al. |
| 8,334,777 B2 | 12/2012 | Wilson et al. |
| 8,384,526 B2 | 2/2013 | Schuman, Sr. et al. |
| 8,598,995 B2 | 12/2013 | Schuman et al. |
| 8,604,917 B2 | 12/2013 | Collins et al. |
| 8,717,181 B2 | 5/2014 | Tallent et al. |
| 8,736,453 B2 | 5/2014 | Wilson et al. |
| 8,779,924 B2 | 7/2014 | Pesot et al. |
| 8,799,011 B2 | 8/2014 | Wilson et al. |
| 9,165,449 B2 | 10/2015 | Ribble et al. |
| 9,230,421 B2 | 1/2016 | Redder et al. |
| 9,492,341 B2 | 11/2016 | Huster et al. |
| 9,552,714 B2 | 1/2017 | Ribble et al. |
| 9,666,061 B2 | 5/2017 | Reeder et al. |
| 9,761,109 B2 | 9/2017 | Ribble et al. |
| 9,978,244 B2 | 5/2018 | Ribble et al. |
| 2007/0210917 A1 | 9/2007 | Collins, Jr. et al. |
| 2009/0212925 A1 | 8/2009 | Schuman, Sr. et al. |
| 2009/0212926 A1 | 8/2009 | Du et al. |
| 2009/0217080 A1 | 8/2009 | Ferguson et al. |
| 2010/0127866 A1 * | 5/2010 | Klein .................. A61B 5/1113 |
| | | 340/541 |
| 2011/0085423 A1 * | 4/2011 | Cottrell ................. G04C 21/02 |
| | | 368/250 |
| 2011/0208541 A1 | 8/2011 | Wilson et al. |
| 2016/0125716 A1 * | 5/2016 | Ribble ............... G08B 21/0461 |
| | | 340/573.4 |
| 2016/0148489 A1 * | 5/2016 | Reeder ................ A61B 5/0002 |
| | | 340/501 |
| 2016/0193095 A1 * | 7/2016 | Roussy ................. A61G 7/002 |
| | | 5/11 |
| 2016/0350489 A1 * | 12/2016 | Ribble ................... G06Q 50/24 |
| 2017/0323555 A1 | 11/2017 | Embree et al. |

* cited by examiner

BED-BASED SAFETY PROTOCOL CONTROL

The present application claims the benefit, under 35 U.S.C. § 119(e), of U.S. Provisional Application No. 62/538,090, which was filed Jul. 28, 2017, and which is hereby incorporated by reference herein in its entirety.

BACKGROUND

The present disclosure relates to patient beds and particularly, to patient beds that monitor one or more bed conditions as part of a safety protocol. More particularly, the present disclosure relates to control of how and when the bed conditions are monitored in accordance with the safety protocol.

Patient beds are used in hospitals, nursing homes, and other types of healthcare facilities. Some patient beds send bed status data to a nurse call system. If any of the bed status data is indicative of an undesirable bed condition, an alert is generated by a nurse call computer and displayed on a display screen at a master nurse station. Some nurse call systems also may send a message to a wireless communication device such as a pager or smart phone carried by one or more caregivers assigned to the patient or room from which the alert originated. A dome light outside the patient's room may also be illuminated to indicate the alert condition.

Protocols have been developed for monitoring only a subset of the overall set of bed status conditions for alerting. Thus, for alerting purposes, some bed status conditions may be ignored. In this regard, see U.S. Pat. No. 7,319,386 which shows and describes a nurse call system in which a master nurse station computer is used to set up Care Alert templates in which certain bed status conditions are selected for alert monitoring and some are not. The master nurse station computer receives the incoming bed status data and determines whether to generate an alert which is to be sent to one or more caregivers. Such a system is available commercially from Hill-Rom Company, Inc. as the NAVICARE® Nurse Call (NNC) System.

Some healthcare facilities may not include a nurse call system or may not include a nurse call system that is configured to receive bed status data from patient beds. However, the caregivers at such healthcare facilities may wish to achieve bed status monitoring of only a subset of the overall number of conditions of a patient bed that are available for monitoring. In some instances, different protocols for monitoring respective subsets of bed conditions based on a patient's needs may be desired. Thus, there is a need for patient beds that have the capability for based-based safety protocol control.

SUMMARY

An apparatus, system, or method may comprise one or more of the features recited in the appended claims and/or the following features which, alone or in any combination, may comprise patentable subject matter:

According to an aspect of the present disclosure, a patient bed may be provided for use in a healthcare facility that may have a network which may include a real time locating system (RTLS) and an electronic medical records (EMR) computer. The patient bed may include a frame, a graphical user interface (GUI) that may be coupled to the frame, and bed control circuitry that may be coupled to the frame and to the GUI. The bed control circuitry may be configured to receive protocol messages from the EMR computer via the bed connector and may enable at least one bed safety protocol in which at least one bed condition may be monitored by the bed control circuitry. The bed control circuitry may generate an alert in response to the at least one bed condition being in an undesirable state and no caregiver being present in the patient room as determined by the RTLS. The bed control circuitry may suspend monitoring the at least one bed condition in response to the RTLS indicating to the control circuitry of the patient bed that at least one caregiver may be present in the patient room.

In some embodiments, the GUI may display a screen having an icon that may indicate whether the at least one bed safety protocol is enabled. Alternatively or additionally, the GUI may display an icon that may be used to manually disable further monitoring of the at least one bed condition of the at least on bed safety protocol.

Optionally, the at least one bed safety protocol may include a falls risk protocol which, when enabled, may require that a patient position monitoring system is monitoring patient position on the frame, may require that an upper frame portion of the frame is in a lowest position relative to a base portion of the frame, may require that one or more bed siderails of the frame are in a raised position, and may require that caster brakes of casters coupled to the frame are set.

In some embodiments, the at least one bed safety protocol may include a pulmonary protocol which, when enabled, may require a head section of a mattress support deck of the frame to be elevated above a threshold angle. The threshold angle may be about 30 degrees, for example. Alternatively or additionally, the at least one bed safety protocol may include a skin protocol which, when enabled, requires the patient to move on the frame by a threshold amount so as not to be stationary for a threshold amount of time.

In some embodiments, therefore, the at least one bed safety protocol may include at least three bed safety protocols. If desired, three alert lights may be coupled to the frame. Each alert light of the three alert lights may correspond to a respective one of the three bed safety protocols. Each alert light of the three alert lights may be illuminated a first color when the respective bed safety protocol is enabled and the at least one bed condition of the respective bed safety protocol is in a desirable state. Each alert light of the three alert lights may be illuminated a second color when the respective bed safety protocol is enabled and the at least one bed condition of the respective bed safety protocol is in an undesirable state. Optionally, each alert light of the three alert lights may be turned off when the respective bed safety protocol is disabled. The frame may extend between a head end and a foot end and the three alert lights may be coupled to the foot end of the frame.

In some embodiments, the at least one bed safety protocol in which at least one bed condition is monitored by the bed control circuitry may be enabled only if a patient position monitoring system coupled to the frame senses that a patient is present on the patient bed. If desired, the bed control circuitry may suspend monitoring the at least one bed condition for a threshold period of time such that, after the threshold period of time, the at least one bed safety protocol may be re-enabled by the bed control circuitry. If desired, the GUI may display an input that is used to command the bed control circuitry to extend the threshold period of time. After the safety protocol has been suspended, the at least one bed safety protocol may be re-enabled by the bed control circuitry in response to the RTLS indicating to the bed control circuitry that the at least one caregiver may have left the patient room even if the threshold period of time has not yet been reached.

In some embodiments in which no threshold period of time is provided, after the safety protocol has been suspended, the at least one bed safety protocol may be re-enabled by the bed control circuitry in response to the RTLS indicating to the bed control circuitry that the at least one caregiver has left the patient room. The bed control circuitry may communicate with the RTLS and the EMR computer via a wired connection from the bed to a connector located in the patient room. Alternatively or additionally, the bed control circuitry may communicate with the RTLS and the EMR computer via wireless transmissions within the patient room.

According to another aspect of the present disclosure, a bed alert system may be provided for use in a healthcare facility that may have a network which may include a real time locating system (RTLS) and an electronic medical records (EMR) computer. The bed alert system may include a patient bed that may have a frame, a graphical user interface (GUI) that may be coupled to the frame, and bed control circuitry that may be coupled to the frame and to the GUI. The bed alert system may also have a bed connector that may be at a fixed location in a patient room in which the patient bed is located. The bed connector may be in communication with the bed control circuitry. The bed connector may operate as a communication link through which messages may be sent from the patient bed to the network and through which messages may be received by the bed from the network. The bed control circuitry may be configured to receive at least one protocol message from the EMR computer via the bed connector and, in response to the at least one protocol message, may enable at least one bed safety protocol in which at least one bed condition may be monitored by the bed control circuitry. The bed control circuitry may generate an alert in response to the at least one bed condition being in an undesirable state and no caregiver being present in the patient room as determined by the RTLS and communicated to the bed control circuitry. The bed control circuitry may suspend monitoring the at least one bed condition in response to the RTLS indicating to the bed control circuitry via the bed connector that at least one caregiver may be present in the patient room.

In some embodiments, the GUI may display a screen that may have an icon that may indicate whether the at least one bed safety protocol is enabled. Alternatively or additionally, the GUI may display an icon that may be used to manually disable further monitoring of the at least on bed safety protocol.

In some embodiments, the at least one bed safety protocol may include a falls risk protocol which, when enabled, may require that a patient position monitoring system is monitoring patient position on the patient bed, may require that an upper frame of the patient bed is in a lowest position relative to a base frame of the patient bed, may require that one or more bed siderails are in a raised position, and may require that caster brakes of the bed are set.

Alternatively or additionally, the at least one bed safety protocol may include a pulmonary protocol which, when enabled, may require a head section of a mattress support deck of the frame to be elevated above a threshold angle. The threshold angle may be about 30 degrees, for example. Further alternatively or additionally, the at least one bed safety protocol may include a skin protocol which, when enabled, may require the patient to move on the bed by a threshold amount so as not to be stationary for a threshold amount of time.

In some embodiments of the bed alert system, therefore, the at least one bed safety protocol may include at least three bed safety protocols. Optionally, three alert lights may be coupled to the frame. Each alert light of the three alert lights may correspond to a respective one of the three bed safety protocols. Each alert light of the three alert lights may be illuminated a first color when the respective bed safety protocol is enabled and the at least one bed condition of the respective bed safety protocol is in a desirable state. If desired, each alert light of the three alert lights may be illuminated a second color when the respective bed safety protocol is enabled and the at least one bed condition of the respective bed safety protocol is in an undesirable state. Optionally, each alert light of the three alert lights may be turned off when the respective bed safety protocol is disabled. The patient bed may extend between a head end and a foot end and the three alert lights may be coupled to the foot end of the patient bed.

In some embodiments, the at least one bed safety protocol in which at least one bed condition is monitored by the bed control circuitry may be enabled only if a patient position monitoring system of the patient bed senses that a patient is present on the patient bed. In some embodiments, the bed control circuitry may suspend monitoring the at least one bed condition for a threshold period of time such that, after the threshold period of time, the at least one bed safety protocol may be re-enabled by the bed control circuitry. The GUI may display an input that may be used to command the bed control circuitry to extend the threshold period of time.

After the safety protocol has been suspended, the at least one bed safety protocol may be re-enabled by the bed control circuitry in response to the RTLS indicating to the control circuitry of the patient bed via the bed connector that the at least one caregiver may have left the patient room even if the threshold period of time has not yet been reached. In some embodiments in which no threshold period of time is provided, after the safety protocol has been suspended, the at least one bed safety protocol may be re-enabled by the bed control circuitry in response to the RTLS indicating to the control circuitry of the patient bed via the bed connector that the at least one caregiver may have left the patient room.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
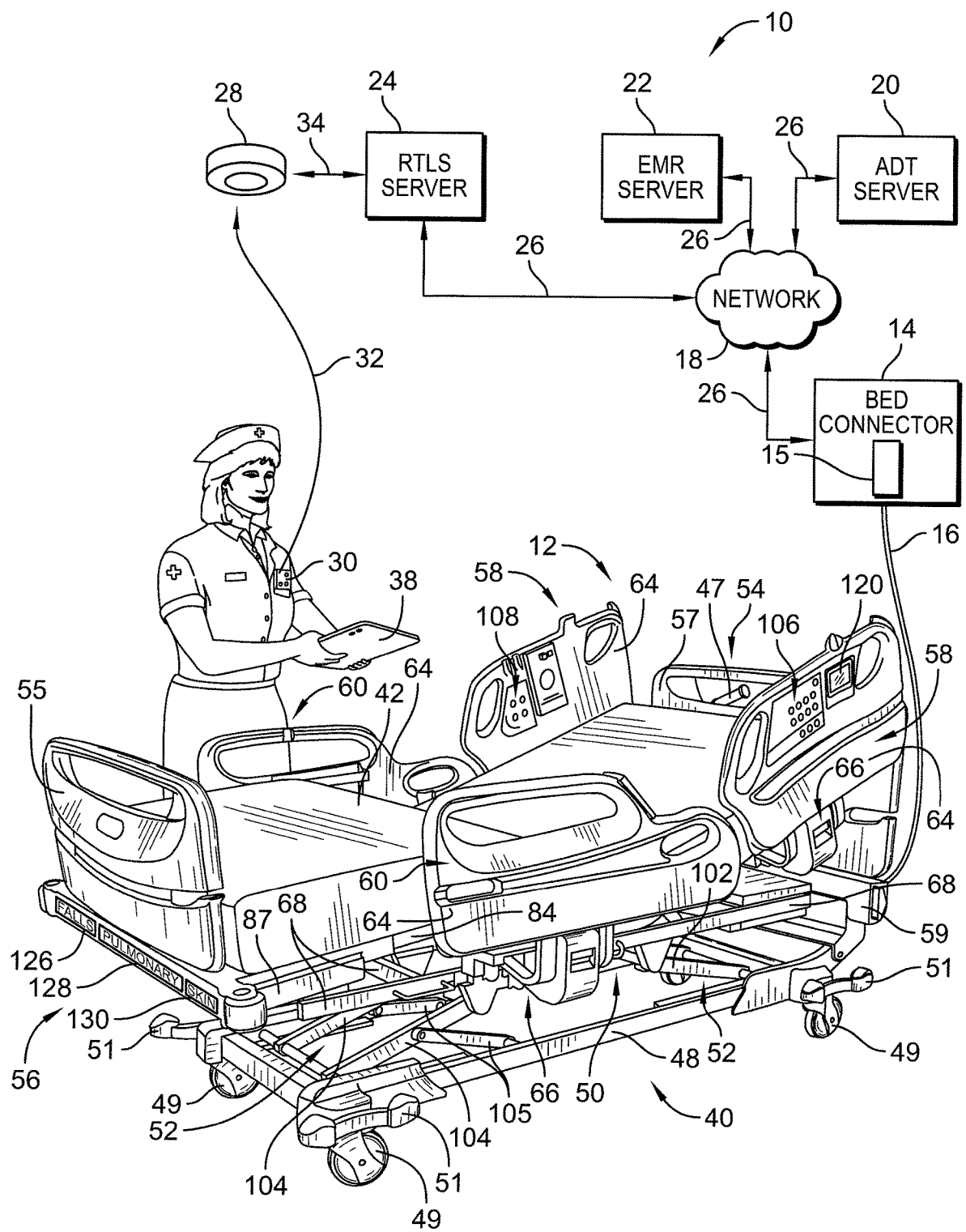
FIG. 1 is diagrammatic view of a bed alert system showing a patient bed coupled to a network via a bed connector; the bed being in communication with an admission/discharge/transfer (ADT) server, an electronic medical records (EMR) server, and a real time locating system (RTLS) server via the network; and a receiver of the RTLS being coupled to the RTLS server and in communication with a locating badge carried by a caregiver that is located alongside the patient bed.

A bed alert system 10 includes a patient bed 12 which is coupled to a bed connector unit 14 in a patient room. In the illustrative example, bed 12 is coupled to unit 14 with a cable 16 such as a cable having 37-pin connectors at its opposite ends as is known in the art. In other embodiments, a wireless connection is made between bed 12 and unit 14. Examples of suitable units 14 for use with bed 12 include bed interface units (BIU's), network interface unit (NIU's), and wireless interface unit (WIU's) available from Hill-Rom Company, Inc. of Batesville, Ind. Further details of BIU's and NIU's are shown and described in U.S. Pat. Nos. 7,538,659 and 7,319,386 and in U.S. Patent Application Publication Nos. 2009/0217080 A1, 2009/0212925 A1 and 2009/0212926 A1, each of which are hereby expressly incorporated by reference herein. Further details of WIU's are shown and described in U.S. Patent Application Publication No. 2007/0210917 A1 which is hereby expressly incorporated by reference herein.

Other types of bed connector units 14 are also within the scope of this disclosure including, but not limited to, the communications hub (aka "Universal Collector") shown and described in connection with FIGS. 11A-18 of U.S. application Ser. No. 15/498,426 which was filed Apr. 26, 2017 and which is hereby incorporated herein by reference herein. Therefore, the bed connector unit 14 shown in FIG. 1 is intended to represent all types of connectors that are used to receive bed status data from bed 12 and to communicate data from one or more other computer devices to bed 12. Accordingly, bed connector unit 14 is coupled to a network 18 of a healthcare facility. As shown diagrammatically in FIGS. 1 and 2, an admission/discharge/transfer (ADT) server 20 of a corresponding ADT system 21, an electronic medical records (EMR) server 22 of a corresponding EMR system 23, and a real time locating system (RLTS) server 24 of a corresponding RTLS 25 are each coupled to network 18. Double headed arrows 26 in FIG. 1 represent the bidirectional communication links between network 18, unit 14 and each of servers 20, 22, 24 and therefore, with each other.

Communication links 26 include wired communication links or wireless communication links at the option of the designer of system 10 in any given healthcare facility. Thus, in some embodiments, bed connector 14 includes wireless communication circuitry 15. Circuitry 15 communicates wirelessly with patient bed 12 and/or with network 18 such as through a wireless access point (WAP)(not shown) of network 18. Such wireless communication contemplated by this disclosure includes Bluetooth (BT), Bluetooth Low Energy (BLE), Zigbee, Z-Wave, and WiFi (e.g., any of the 802.11$_x$ protocols). However, it should be understood that all types of wireless communication are within the scope of the present disclosure, including infrared (IR) communications, ultrasonic (US) communications, and so forth. In some embodiments in which bed 12 communicates wirelessly with bed connector 14, cable 16 is omitted.

The RTLS 25 of system 10 includes wireless transceiver units 28 placed throughout the healthcare facility. Only one such unit 28 is depicted diagrammatically in FIG. 1. The RTLS 25 of system 10 also includes caregiver locating or tracking tags or badges 30 that are worn by caregivers. Each of the transceiver units 28 receives a wireless signal from the badges 30 of each of the caregivers wearing badges 30 and that are within communication range of the respective unit 28 as indicated diagrammatically by arrow 32 in FIG. 1. The wireless signal from each badge 30 includes badge identification data (ID) which is unique to the corresponding badge 30. Unit 28 then transmits its ID, which corresponds to a particular location in the healthcare facility, and the badge (ID) to RTLS server as indicated diagrammatically by a bidirectional communication link 34 in FIG. 1.

Bed 12 includes a patient support structure such as a frame 40 that supports a surface or mattress 42 as shown in FIG. 1. As compared to prior art beds, bed 12 includes patient safety protocol screens that permit various patient safety protocols to be enabled and disabled on bed 12. The screens shown in FIGS. 3 and 4 relate to the patient safety protocols of bed 12. It should be understood that FIG. 1 shows some details of one possible bed 12 having patient safety protocol capability. However, this disclosure is applicable to other types of patient support apparatuses, including other types of beds, surgical tables, examination tables, stretchers, chairs, wheelchairs, patient lifts and the like.

The NAVICARE® Nurse Call (NNC) system available from Hill-Rom Company, Inc. allows caregivers to configure Care Alert templates remotely from the patient beds and then monitor incoming bed status data to see if any alarm or alert conditions of any enabled Care Alert templates are detected. If they are, then one or more alert notifications to caregivers are generated. Such alert notifications include, for example, sending a message to a wireless communication device (e.g., pager, smart phone, tablet computer, telephone handset, etc.) carried by an assigned caregiver or lighting up a dome light situated outside the patient room having the bed with the alert condition. See U.S. Pat. No. 7,319,386 for additional details of the Care Alert template capability of the NNC system. The words "alert" and "alarm" are used interchangeably herein and each is intended to have the broad meaning of both. In FIG. 1, the caregiver is shown carrying a tablet computer 38. Some healthcare facilities do not have the NNC system, but instead may have no nurse call system or may have a third party nurse call system which is not capable of receiving bed status data from patient beds 12. In such arrangements in the prior art, it has not been possible to configure the patient beds 12 according to particular patient safety protocols like those described below.

Still referring to FIG. 1, frame 40 of bed 12 includes a base frame 48 (sometimes just referred herein to as a base 48), an upper frame assembly 50 and a lift system 52 coupling upper frame assembly 50 to base 48. Lift system 52 is operable to raise, lower, and tilt upper frame assembly 50 relative to base 48. Bed 12 has a head end 54 and a foot end 56. Patient bed 12 further includes a footboard 55 at the foot end 56 and a headboard 57 at the head end 54. Illustrative bed 12 includes a pair of push handles 47 coupled to an upstanding portion 59 of base 48 at the head end 54 of bed 12. Only a portion of one push handle 47 can be seen in FIG. 1. Headboard 57 is coupled to upstanding portion 59 of base as well. Foot board 55 is coupled to upper frame assembly 50. Base 48 includes wheels or casters 49 that roll along floor (not shown) as bed 12 is moved from one location to another. A set of foot pedals 51 are coupled to base 48 and are used to brake and release casters 49.

Illustrative patient bed 12 has four siderail assemblies coupled to upper frame assembly 50 as shown in FIG. 1. The four siderail assemblies include a pair of head siderail assemblies 58 (sometimes referred to as head rails) and a pair of foot siderail assemblies 60 (sometimes referred to as foot rails). Each of the siderail assemblies 58 and 60 is movable between a raised position, as shown in FIG. 1, and a lowered position (not shown). Siderail assemblies 58, 60 are sometimes referred to herein as siderails 58, 60. Each siderail 58, 60 includes a barrier panel 64 and a linkage 66. Each linkage 66 is coupled to the upper frame assembly 50 and is configured to guide the barrier panel 64 during movement of siderails 58, 60 between the respective raised and lowered positions. Barrier panel 64 is maintained by the linkage 66 in a substantially vertical orientation during movement of siderails 58, 60 between the respective raised and lowered positions.

Figure 2:
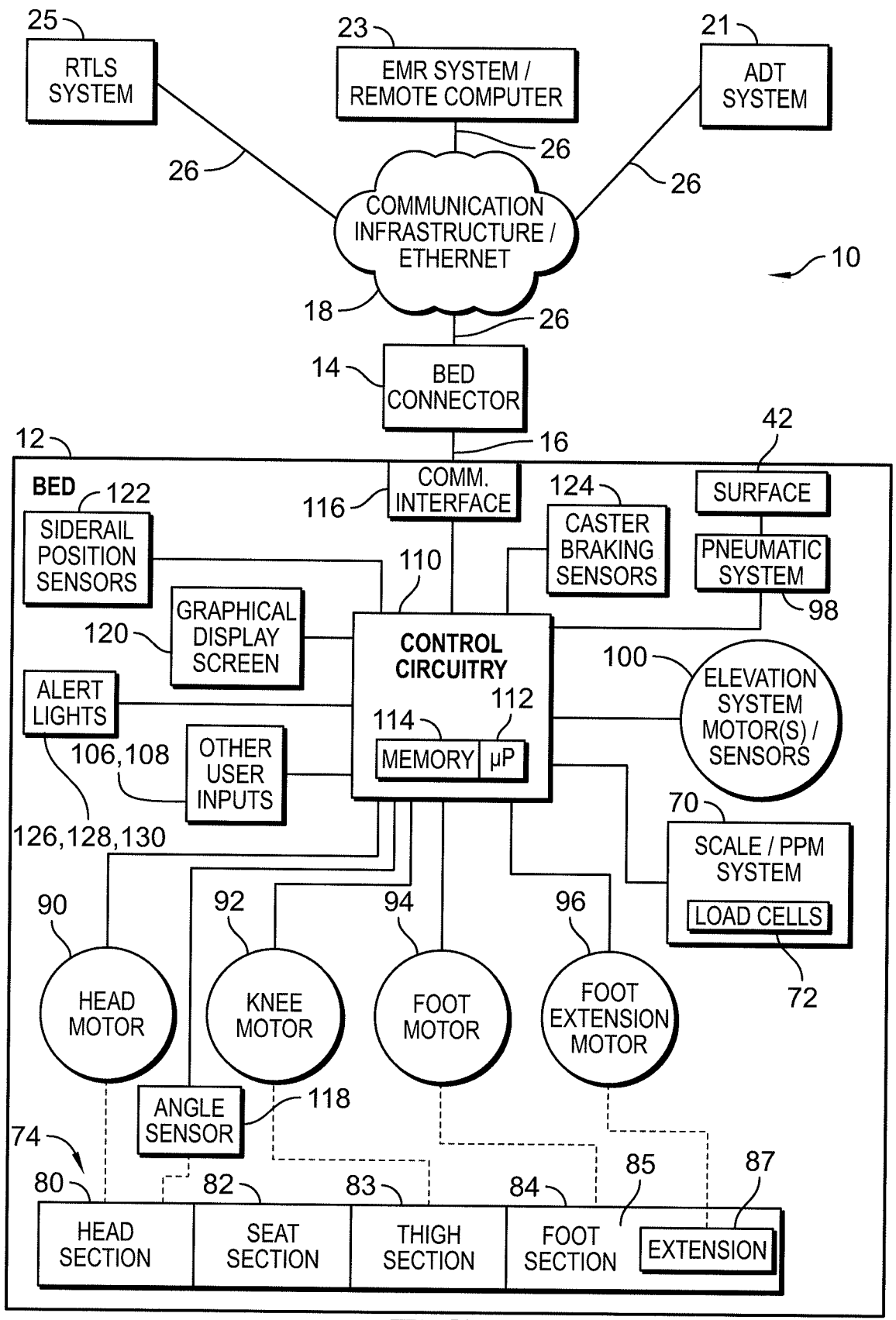
FIG. 2 is a block diagram showing various components of the patient bed.

Upper frame assembly 50 includes various frame elements 68 that form, for example, a lift frame and a weigh frame supported with respect to the lift frame by a set of load cells 72 of a scale and/or patient position monitoring (PPM) system 70 of bed 12. A patient support deck 74, shown diagrammatically in FIG. 2, is carried by the weigh frame portion of upper frame assembly 50 and supports mattress 42 thereon. Patient support deck 74 includes a head section 80, a seat section 82, a thigh section 83 and a foot section 84 in the illustrative example as shown diagrammatically in FIG. 2. Sections 80, 83, 84 are each movable relative to the weigh frame portion of upper frame assembly 50. For example, head section 80 pivotably raises and lowers relative to seat section 82 whereas foot section 84 pivotably raises and lowers relative to thigh section 83. Additionally, thigh section 83 articulates relative to seat section 82. Also, in some embodiments, foot section 84 is extendable and retractable to change the overall length of foot section 84 and therefore, to change the overall length of deck 74. For example, foot section 84 includes a main portion 85 and an extension 87 in some embodiments as shown diagrammatically in FIG. 2.

In the illustrative embodiment, seat section 82 is fixed in position with respect to the weigh frame portion of upper frame assembly 50 as patient support deck 74 moves between its various patient supporting positions including a horizontal position to support the patient in a supine position, for example, and a chair position (not shown) to support the patient in a sitting up position. In other embodiments, seat section 82 also moves relative to upper frame assembly 50, such as by pivoting and/or translating. Of course, in those embodiments in which seat section 82 translates relative to the upper frame assembly 50, the thigh and foot sections 83, 84 also translate along with seat section 82. As bed 12 moves from the horizontal position to the chair position, foot section 84 lowers relative to thigh section 83 and shortens in length due to retraction of the extension 87 relative to main portion 85. As bed 12 moves from the chair position to the horizontal position, foot section 84 raises relative to thigh section 83 and increases in length due to extension of the extension 87 relative to main portion 85. Thus, in the chair position, head section 80 extends upwardly from upper frame assembly 50 and foot section 84 extends downwardly from thigh section 83.

As shown diagrammatically in FIG. 2, bed 12 includes a head motor or actuator 90 coupled to head section 80, a knee motor or actuator 92 coupled to thigh section 83, a foot motor or actuator 94 coupled to foot section 84, and a foot extension motor or actuator 96 coupled to foot extension 87. Motors 90, 92, 94, 96 may include, for example, an electric motor of a linear actuator. In those embodiments in which seat section 82 translates along upper frame assembly 50 as mentioned above, a seat motor or actuator (not shown) is also provided. Head motor 90 is operable to raise and lower head section 80, knee motor 92 is operable to articulate thigh section 83 relative to seat section 82, foot motor 94 is operable to raise and lower foot section 84 relative to thigh section 83, and foot extension motor 96 is operable to extend and retract extension 87 of foot section 84 relative to main portion 85 of foot section 84.

In some embodiments, bed 12 includes a pneumatic system 98 that controls inflation and deflation of various air bladders or cells of mattress 42. The pneumatic system 98 is represented in FIG. 2 as a single block but that block 98 is intended to represent one or more air sources (e.g., a fan, a blower, a compressor) and associated valves, manifolds, air passages, air lines or tubes, pressure sensors, and the like, as well as the associated electric circuitry, that are typically included in a pneumatic system for inflating and deflating air bladders of mattresses.

As also shown diagrammatically in FIG. 2, lift system 52 of bed 10 includes one or more elevation system motors or actuators 100, which in some embodiments, comprise linear actuators with electric motors. Thus, actuators 100 are sometimes referred to herein as motors 100. Alternative actuators or motors contemplated by this disclosure include hydraulic cylinders and pneumatic cylinders, for example. The motors 100 of lift system 52 are operable to raise, lower, and tilt upper frame assembly 50 relative to base 48. In the illustrative embodiment, one of motors 100 is coupled to, and acts upon, a set of head end lift arms 102 and another of motors 100 is coupled to, and acts upon, a set of foot end lift arms 104 to accomplish the raising, lowering and tilting functions of upper frame 50 relative to base 48. Guide links 105 are coupled to base 48 and to lift arms 104 in the illustrative example as shown in FIG. 1. Lift system 52 of bed 12 is substantially similar to the lift system of the VERSACARE® bed available from Hill-Rom Company, Inc. Other aspects of bed 12 are substantially similar to the bed shown and described in more detail in International Publication No. WO 2016/196403 A1 which is hereby expressly incorporated by reference herein.

Each of siderails 58 includes a first user control panel 106 coupled to the outward side of the associated barrier panel 64. Controls panels 106 include various buttons that are used by a caregiver to control associated functions of bed 12. For example, control panel 106 includes buttons that are used to operate head motor 90 to raise and lower the head section 80, buttons that are used to operate knee motor 92 to raise and lower the thigh section 83, and buttons that are used to operate motors 100 to raise, lower, and tilt upper frame assembly 50 relative to base 48. In some embodiments, control panel 106 also includes buttons that are used to operate motor 94 to raise and lower foot section 84 and buttons that are used to operate motor 96 to extend and retract foot extension 87 relative to main portion 85. Each of siderails 58 also includes a second user control panel 108 coupled to the inward side of the associated barrier panel 64. Controls panels 108 include various buttons that are used by a patient to control associated functions of bed 12. In some embodiments, the buttons of control panels 108, 108 comprise membrane switches that are used to control head motor 90 and knee motor 92.

As shown diagrammatically in FIG. 2, bed 12 includes control circuitry 110 that is electrically coupled to motors 90, 92, 94, 96 and to motors 100 of lift system 52. Control circuitry 110 is represented diagrammatically as a single block in FIG. 2, but control circuitry 110 in some embodiments, comprises various circuit boards, electronics modules, and the like that are electrically and communicatively interconnected. Control circuitry 110 includes one or more microprocessors 112 or microcontrollers that execute software to perform the various control functions and algorithms described herein. Thus, circuitry 110 also includes memory 114 for storing software, variables, calculated values, and the like as is well known in the art.

As also shown diagrammatically in FIG. 2, a user inputs block represents the various user inputs such as buttons of control panels 106, 108, for example, that are used by the caregiver or patient to communicate input signals to control circuitry 110 of bed 12 to command the operation of the various motors 90, 92, 94, 96, 100 of bed 12, as well as commanding the operation of other functions of bed 12. Bed 12 includes at least one graphical user input (GUI) or display screen 120 coupled to a respective siderail 58 as shown in FIG. 1. Display screen 120 is coupled to control circuitry 110 as shown diagrammatically in FIG. 2. In some embodiments, two graphical user interfaces 120 are provided and are coupled to respective siderails 58. Alternatively or additionally, one or more graphical user interfaces are coupled to siderails 60 and/or to one or both of the headboard 57 and footboard 55. Control circuitry 110 receives user input commands from graphical display screen 120 as will be described in further detail below with regard to FIGS. 3 and 4.

In the illustrative embodiment, bed 12 has a communication interface or port 116 which provides bidirectional communication via cable 16 with bed connector 14 which, in turn, communicates bidirectionally with network 18 and the various computers and systems of network 18, such as illustrative servers or computers 21, 23, 25. In other embodiments, communication interface 116 is used for wireless communications with bed connector 14. Communication interface 116 also may be configured for wireless communication with network 18 and its associated devices without the use of bed connector 14 in some embodiments. For example, WiFi communications between communication interface 116 and one or more WAP's of network 18 is contemplated by this disclosure.

Still referring to FIG. 2, bed 12 includes various sensors to sense the states or positions of various portions of bed 12. In the illustrative example, bed 12 includes an angle sensor 118 coupled to head section 80 to sense an angle of head section elevation (sometimes referred to as the head-of-bed (HOB) angle). Angle sensor 118 is an accelerometer (single-axis or multi-axis) in some embodiments. In such embodiments, the HOB angle is measured with respect to a horizontal reference axis and/or with respect to a vertical reference axis depending upon the orientation of the accelerometer relative to head section 80 and depending upon the type of accelerometer. In other embodiments, angle sensor 118 includes a rotary potentiometer which measures the HOB angle between head section 90 and another portion of frame 40 such as one of frame members 68 of upper frame assembly 50. In further embodiments, angle sensor 90 is included in head motor 90 and has an output that correlates to the HOB angle. Motor 90 may include, for example, a shaft encoder, a Hall effect sensor, a rotary potentiometer, or some other sensor which serves as angle sensor 118 of bed 12 in such embodiments. Similar such sensors are included in elevation system motors 100 in some embodiments and are used to determine the position of upper frame assembly 50 relative to base 48 such as the height of upper frame assembly 50 and/or amount of tilt of upper frame assembly 50 relative to base 48.

Bed 12 also includes siderail position sensors 122 to sense the position (e.g., raised and/or lowered) of each of siderails 58, 60 and one or more caster braking sensors 124 to sense whether casters 49 are braked or released. In some embodiments, sensors 122, 124 include limit switches that are engaged or disengaged by a linkage mechanism, such as linkage 66 in the case of siderails 58, 60, to produce output signals indicative of the position of the respective mechanical structure. Alternatively, Hall effect sensors may be used as some or all of sensors 122, 124 in some embodiments. The foregoing types of sensors 122, 124 are just a couple examples of suitable sensors and therefore, this disclosure is intended to cover all types of sensors that may be used as sensors 122, 124. Each of the sensors mentioned above, including sensors internal to motors 100 and sensors 118, 122, 124 are each coupled electrical to control circuitry 110 for analysis and/or processing.

As mentioned above, bed 12 has safety protocol capability. Thus, control circuitry 110 is programmed to enable and disable the safety protocols of bed 12. In the illustrative embodiment discussed herein, control circuitry 110 of bed 12 is configured to implement three different safety protocols, namely, a falls risk protocol (aka a falls protocol), a pulmonary protocol, and a safe skin protocol (aka a skin protocol). It should be understood that these are just examples of possible protocols for implementation on bed 12 and other protocols based on bed status information are within the scope of this disclosure.

As shown in FIG. 1, bed 12 includes three status or alert lights at foot end 56 corresponding to the three protocols. Thus, bed 12 includes a falls alert light 126, a pulmonary alert light 128, and a skin alert light 130. In the illustrative example, alert lights 126, 128, 130 are coupled to a lateral frame member of extension 87 of foot section 84 and are situated beneath footboard 55. In other embodiments, alert lights 126, 128, 130 may be located elsewhere on bed 12 such as on base 48 and/or one or more of siderails 58, 60. In FIG. 2, alert lights 126, 128, 130 are represented diagrammatically as a single block and are coupled electrically to control circuitry 110 to control the manner in which alert lights 126, 128, 130 are illuminated as will be discussed in further detail below.

In some embodiments, alert lights 126, 128, 130 are illuminated different colors to indicate certain statuses. For example, lights 126, 128, 130 are in turned off if the particular protocol is not enabled, meaning the bed statuses contributing to the particular protocol are not being monitored for a protocol violation. Lights 126, 128, 130 are illuminated a first color, such as green for example, if the associated protocol is enabled, meaning the bed statuses contributing to the particular protocol are being monitored for a protocol violation, but all of the monitored bed statuses for the particular protocol are satisfactory or in a desirable state (i.e., not violated). Lights 126, 128, 130 are illuminated a second color, such as amber or yellow for example, if the associated protocol is enabled and at least one of the monitored bed statuses for the particular protocol is undesirable or unsatisfactory (i.e., violated). In some embodiments, an audible alarm of bed 12 may also sound under the control of control circuitry 110 if an unsatisfactory condition of a particular protocol is detected. Lights 126, 128, 130 are illuminated a third color, such as blue for example, if the associated protocol is enabled and at least one of the monitored bed statuses for the particular protocol is undesirable (i.e., violated), but the alert has been suspended as will be discussed in further detail below. If the alert has been suspended, any associated audible alarms may be turned off during the alarm suspension.

In some embodiments, alert lights 126, 128, 130 may be illuminated the second color, yellow for example, continuously in response to an unsatisfactory condition of the associated protocol being detected and may flash on and off in the second color if the alert has been suspended. Alternatively, alert lights 126, 128, 130 may be flashed on and off in the second color, yellow for example, in response to an unsatisfactory condition of the associated protocol being detected and may be illuminated continuously in the second color if the alert has been suspended. In such embodiments, therefore, lights 126, 128, 130 are not illuminated in any third color to indicate the suspension of the alarm of the associated protocol.

As mentioned above, illustrative bed 12 is configured to implement a falls risk protocol, a pulmonary protocol, and a safe skin protocol. According to the falls risk protocol example given herein, PPM system 70 is required to be enabled to monitor a position of the patient relative to the frame 40, upper frame assembly 50 of frame 40 is required to be in a lowest position relative to a base 48 of frame 40 as sensed by sensors of motors 100, siderails 58, 60 of the frame 40 are required to be in the respective raised positions as sensed by siderail position sensors 122, and the caster brake of one or more of casters 49 is required to be braked or set as sensed by caster braking sensors 124. Thus, if PPM system 70 indicates that the patient is moving toward exiting bed 12 by a threshold amount (including exiting the bed 12) such movement beyond the threshold is considered to be a violation of the falls protocol by control circuitry 110 assuming the falls protocol is enabled. Similarly, if upper frame assembly 50 is moved upwardly out of its lowest position, or if any of siderails 58, 60 are moved out of their raised positions, or if the one or more casters 49 are released or unbraked, each of those unwanted conditions is considered to be a violation of the falls protocol by control circuitry 110 assuming the falls protocol is enabled.

According to the pulmonary protocol example given herein, head section 80 of mattress support deck 74 of frame 40 is required to be elevated above a threshold angle as measured by angle sensor 118. The threshold angle may be about 30 degrees, for example. In some embodiments, GUI 120 is used to adjust the threshold angle to an angle greater than 30 degrees (e.g., 45 degrees or 60 degrees) or to an angle less than 30 degrees (e.g., 17 degrees or 10 degrees). Thus, if the HOB angle falls below the threshold angle, that is considered to be a violation of the pulmonary protocol, assuming the pulmonary protocol is enabled. Having the HOB angle above a threshold angle, such as 30 degrees, helps to prevent ventilator assisted pneumonia (VAP) in some patients. Alternatively or additionally, the pulmonary protocol may require that the patient undergo certain pulmonary therapies performed by mattress 42 within certain time intervals. Examples of such pulmonary therapies include, for example, continuous lateral rotation therapy (CLRT) using rotation bladders of mattress 42 and/or percussion/vibration (P&V) therapy using P&V bladders of mattress 42. Thus, CLRT or P&V therapy may be required for ½ hour, 1 hour, 2 hours, etc. twice per day or at least once within in any 8 hour nursing shift according to the pulmonary protocol, just to give a couple of nonlimiting examples.

According to the safe skin protocol example given herein, the patient is required to move relative to the frame 40 by a threshold amount so as not to be stationary for a threshold amount of time. Such movement is detected by the PPM system 70 in the illustrative embodiment. Alternatively or additionally, the safe skin protocol may require the operation of certain features of mattress 42 for certain periods of time or at certain intervals. For example, an alternating pressure feature of mattress 42 may be required to be operating substantially continuously while the patient is in bed 12. Alternating pressure refers to sequentially inflating and deflating every other laterally extending bladder of two sets of interleaved or interdigitated bladders of mattress 12. Alternatively or additionally, the safe skin protocol may require a microclimate management layer or low airloss topper of mattress 42 to have air circulated therethrough to remove or reduce the amount of moisture and/or heat between the patient and the upper surface of mattress 42. Further alternatively or additionally, the safe skin protocol may require that turn assist bladders of the mattress 42 be used from time to time to turn the patient to their left side and to their right side. When the safe skin protocol is enabled, control circuitry 110 monitors the various time thresholds for patient movement, alternating pressure, microclimate management operation, and turn assist, as the case may be.

Figure 3:
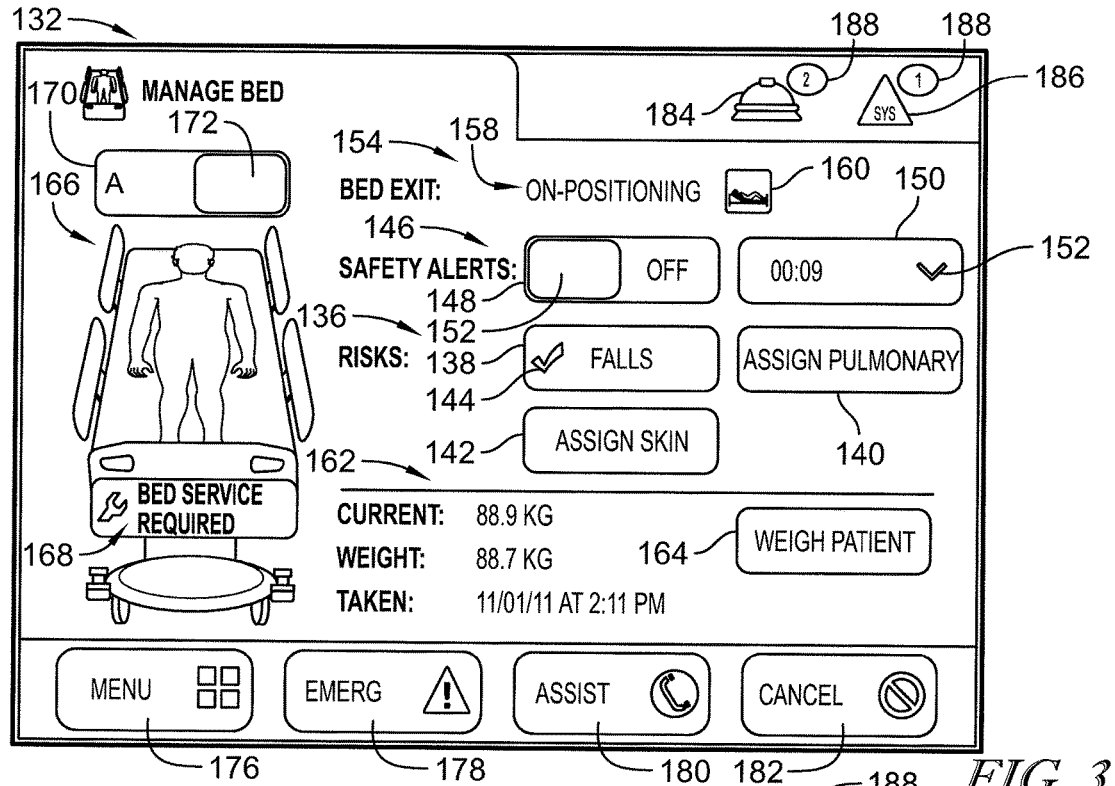
FIG. 3 is a screen shot of a first Manage Bed screen that appears on a graphical user interface (GUI) of the patient bed in response to the RTLS determining that a caregiver with a badge is located in a patient room containing the patient bed, the first Manage Bed screen having a Risks window containing icons associated with Falls, Pulmonary, and Skin bed safety protocols, and the first Manage Bed screen having a Safety Alerts field with an icon indicating whether the bed safety protocol is on (aka enabled) or off (aka disabled)

Referring now to FIG. 3, a first Manage Bed screen 132 that appears on GUI 120 of patient bed 12 in response to the RTLS 25 determining that a caregiver with a badge 30 is located in a patient room containing the patient bed 12 is shown. Prior to RTLS 25 detecting that the caregiver has entered the room having bed 12, GUI 120 is either dormant or shows a home screen. The first Manage Bed screen 132 has a Risks window 136 containing a Falls icon or field 138, a Pulmonary field or icon 140, and a Skin icon or field 142. Fields 138, 140, 142 relate to the respective falls, pulmonary and skin bed safety protocols.

In the illustrative example, a check mark 144 appears in field 138 to indicate that, when the safety alerts of bed 12 are enabled, the set of criteria for the falls protocol will be monitored by control circuitry 110 of bed 12. Also in the illustrative example, the text "Assign Pulmonary" appears in field 140 and the text "Assign Skin" appears in field 142 to indicate that the pulmonary and skin protocols will not be monitored by control circuitry 110 of bed 12 when the safety alert monitoring feature of bed 12 is enabled. If desired, a caregiver can select or touch fields 140, 142 to designate the pulmonary and skin protocols, respectively, for monitoring when the safety alerts are enabled. If fields 140, 142 are selected, a check mark similar to check mark 114 of field 138 appears in the respective field 140, 142. If one of fields 138, 140, 142 having a check mark 144 is touched, then the respective falls, pulmonary, or skin protocol is deselected from being monitored by control circuitry 110 of bed 12 when the safety alert monitoring feature of bed 12 is enabled. In the illustrative example, if filed 138 is touched, then check mark 144 disappears from field 138 and the text "Assign Falls" appears in field 138.

Figure 4:
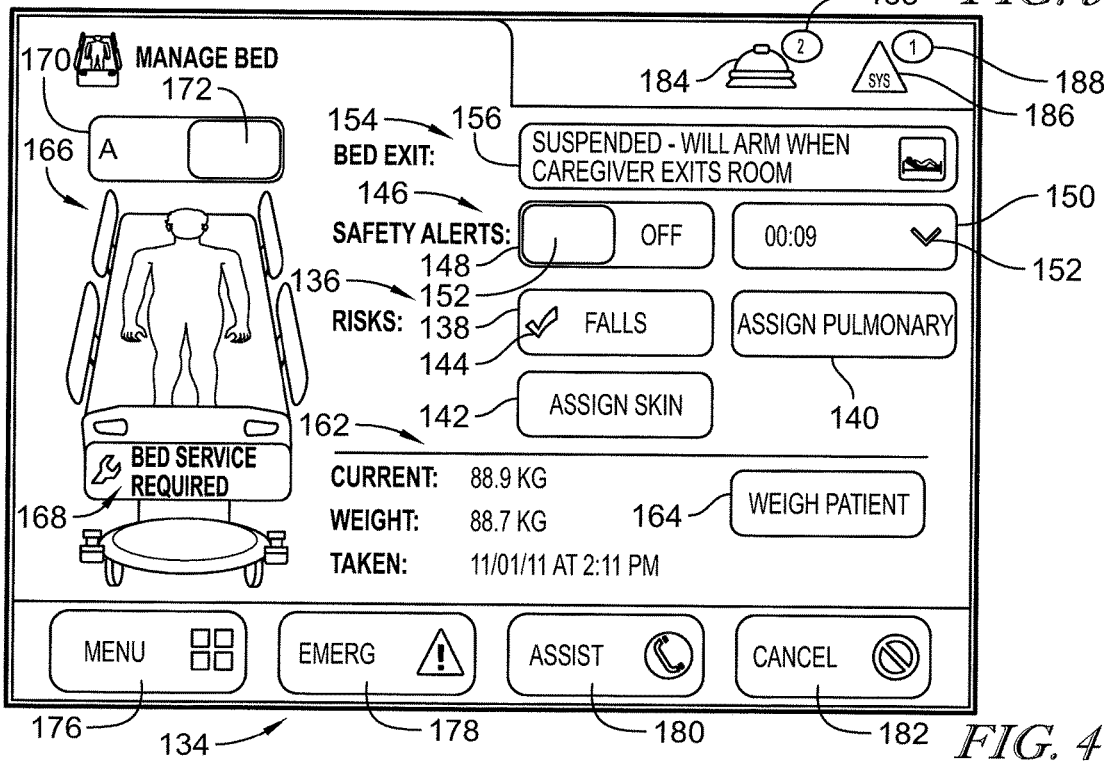
FIG. 4 is a screen shot of a second Manage Bed screen, similar to the first Manage Bed screen of FIG. 3, showing a Bed Exit field having a message indicating that monitoring of bed status condition in accordance with any enabled bed safety protocols has been suspended in response to the RTLS communicating to the patient bed that a caregiver with a badge is present in the patient room with the patient bed.

Screen 132 also has a Safety Alerts window 146 containing an ON/OFF icon or field 148 and a suspend time field 150. Field 148 includes a graphical slider icon 152 which can be touched and dragged between the left side of field 148 and the right side of field 148 to enable and disable, respectively, the safety alert monitoring function of bed 12. As shown in FIGS. 3 and 4, slider icon 152 is located in the left side of field 148 and so the safety alert monitoring functioning of bed 12 is enabled such that control circuitry 110 is monitoring the bed statuses associated with the protocols that have been selected for monitoring in the Risks window 136 (the falls protocol in the illustrative example). The word "OFF" appears in the right side of field 148 to indicate that, if slider icon 148 is moved to the right, the safety alert monitoring function of bed 12 will be turned off or disabled. If slider icon 148 is moved to the right side of field 148, the word "OFF" disappears and the user perceives that icon 148 has covered it up. Also if slider icon 148 is moved to the right side of field 148, the word "ON" appears in the left side of field 148 to indicate that the safety alert monitoring function of bed 12 can be enabled or turned on by moving icon 152 back to the left side of field 148.

According to some embodiments, when RTLS 25 detects that a caregiver wearing badge 30 enters the room in which bed 12 is located, any alerts and/or audible alarms that are being generated by control circuitry 110 of bed 12 as a result of a bed status of a monitored protocol being in an undesirable state, are suspended (i.e., no longer communicated or sounded). The alerts and audible alarms are suspended for the duration of time that the badged caregiver remains in the room having bed 12. Also, in response to a badged caregiver entering the room having bed 12, GUI 120 displays a second Manage Bed screen 134, similar to the first Manage Bed screen 132, but showing a Bed Exit field 154 having a window 156 with a message indicating that monitoring of bed status conditions in accordance with any selected bed safety protocols has been suspended in response to the RTLS 25 communicating to the bed 12 that a caregiver with badge 30 is present in the patient room with bed 12. Other portions of screen 134 are the same as screen 132 and the description herein of those portions of screen 132 is equally applicable to screen 134.

If a caregiver who is not wearing any badge 30 enters the room having bed 12, any alerts and/or audible alarms that are being generated by control circuitry 110 of bed 12 as a result of a bed status of a monitored protocol being in an undesirable state, can be suspended manually by touching field 150. Field 150 displays an amount of time in hours:minutes format that the safety alert monitoring function of bed 12 will be suspended in response to selection of field 150. In the illustrative example, the manual suspension time is 9 minutes. After the designated suspension interval expires, any alerts and/or alarms will again be generated by control circuitry 110 of bed 12 if the unsatisfactory conditions of bed 12 have not been rectified during the suspension time. In such circumstances, filed 150 can be selected again to start another suspension interval running. Alternatively or additionally, the alerts and alarms can be suspended manually for the designated suspension time by sliding icon 152 in field 148 from the left side "ON" position to the right side "OFF" position. If icon 152 is moved in this manner while an alert or alarm condition is detected, then the icon 152 will automatically move back to the left side "ON" position after the suspension interval expires if the unsatisfactory conditions of bed 12 have not been rectified during the suspension time. Field 150 also contains an arrow icon 152 that is selected to cause a menu to appear for changing the suspension time.

In some embodiments, the suspension timer of field 150 is used even when the one or more enabled safety protocols have been suspended in response to presence of a badged caregiver in the room having bed 12 as detected by the RTLS 25. In such embodiments, if the badged caregiver is still in the room after the suspension time expires, the safety protocols are re-enabled and appropriate alerts or alarms generated if the undesirable conditions of the one or more enabled protocols have not been rectified. In some embodiments, after the one or more safety protocols have been suspended, the at least one bed safety protocol is re-enabled by control circuitry 110 in response to the RTLS 25 indicating to the control circuitry 110 of bed 12 via the bed connector 14 that the badged caregiver has left the patient room even if the threshold period of time in field 150 has not yet been reached.

In the illustrative example of FIG. 3, Bed Exit field 154 of screen 132 includes PPM mode text 158 and a PPM mode icon 160. As alluded to above, PPM system 70 has different levels of sensitivities or modes for monitoring patient movement on bed 12. In some embodiments, PPM system 70 of bed 12 has three modes but any number of modes are contemplated by this disclosure. The three modes of the illustrative embodiment include a patient movement mode, a patient positioning mode, and a bed exiting mode. The patient movement mode is the most sensitive and results in an alarm if PPM system 70 detects a small amount of patient movement such as the patient sitting up in bed 12 or rolling over toward one side of bed 12 of the other. The patient positioning mode is an intermediate mode that results in an alarm if PPM system 70 detects a patient moving close to the side edge bed 12 in preparation for potentially exiting the bed 12. The exiting mode is the least sensitive mode and results in an alarm if the PPM system 70 detects that the patient has moved all the way to the side edge of the bed 12 or has transferred some of their weight off of the bed 12 during the process of exiting the bed 12. In the illustrative example, message 158 indicates that the PPM system 70 is "ON" and is in the "POSITIONING" mode. Each of the three PPM system modes has its own icon and so icon 160 is the one that corresponds to the positioning mode.

In some embodiments of system 10, control circuitry 110 of bed 12 receives one or more messages from EMR system 23 and/or ADT system 21 which results in the safety protocol monitoring functionality of bed 12 being enabled automatically. Such messages indicate to control circuitry 110 of bed 12 which of the falls, pulmonary, and skin protocols are to be monitored and also indicate to bed 12 the PPM mode in which PPM system 70 is to be operated according to the associated protocol. The EMR or ADT system determines which safety protocols to implement at bed 12 based on patient data such as the patient's medical condition, age, weight, and/or medical procedure performed, or to be performed, on the patient, for example.

In some embodiments, bed 12 is not able to communicate with ADT system 21 and EMR system 23 in which case, the safety protocols are selected manually by a caregiver using buttons 138, 140, 142 at bed 12 and are enabled manually at bed 12 using slider icon 152 in field 148 as described above. Furthermore, in some embodiments, bed 12 is not able to communicate with RTLS 25 in which case, screen 134 does not appear automatically when a badged caregiver enters the room in which bed 12 is situated and therefore, any alarm suspension by the badged caregiver is carried out in the same manner described above in connection with caregivers not having badges 30.

If the falls prevention protocol is not selected, but if one or the other or both of the pulmonary and skin protocols are selected, then bed 12 automatically suspends any alerts or alarms associated with those protocols if the patient gets out of bed 12 as detected by PPM system 70. In other words, if the patient is not in bed 12, further monitoring according to the pulmonary or skin protocols is not needed. When the patient gets back in bed 12 as detected by PPM system 70, any of the previously enabled but suspend protocols, are re-enabled based on patient presence on bed 12.

Screen 132 also has a Weighing window 162 which shows a patient's current weight as measured by scale system 70. Window 162 also shows the most recent weight reading for the patient that has been stored in control circuitry 110 of bed 12 and/or in the patient's EMR and the date and time at which the most recent weight reading was taken. In the illustrative example, the patient's current weight is 88.9 kilograms (KG), the most recent stored weight reading is 88.7 KG and was taken on Nov. 1, 2011 at 2:11 pm. Window 162 also includes a WEIGH PATIENT button 164 that is touched or selected to take the read the patient's current weight reading for storage on bed 12 and/or in the patient's EMR.

Illustrative screen 132 includes a bed icon 166 with a "BED SERVICE REQUIRED" message 168 shown in the footboard portion of icon 166. When bed service of any type is needed, the footboard around message 168 turns from a first color, such as gray or beige, to a second color such as yellow or red and, in some embodiments, flashes. Alternatively, the message 168 is absent if no bed service is required and then appears in icon 166 when bed service is required. In some embodiments, icon 166 shows an image of a patient on the bed when PPM system 70 detects the presence of the patient on bed 12 and the image of the patient is removed from icon 166 when the patient exits the bed 12.

In some embodiments, system 10 includes a nurse call system, such as the HILL-ROM® NNC system or a third party nurse call system, which is communicatively compatible with bed 12. That is, hardware of the compatible nurse call system, such as master nurse stations, graphical room stations, staff stations, nurse call servers, and the like, are able to send messages to bed 12 and receive messages from bed 12 via bed connector 14, for example. Such a nurse call system may be coupled to bed connector 14 through network 18 or separately through dedicated wiring or infrastructure. The remote computer portion of block 23 in FIG. 2 may be considered to diagrammatically represent a nurse call system in lieu of or in addition to the EMR system representation by block 23. Additional details of suitable nurse call equipment that may be included in system 10 are shown and described in U.S. Pat. Nos. 8,598,995; 8,384,526; 8,169,304; 8,046,625 and 7,319,386; each of which is hereby incorporated by reference herein to the extent not inconsistent with the present disclosure which shall control as to any inconsistencies.

In some embodiments of system 10 having a nurse call system compatible with bed 12, screens 132, 134 appear on a graphical room station in the room in which bed 12 is located rather than appearing on GUI 120 of bed 12. The graphical room station communicates with bed 12 via bed connector 14. In a semi-private room having two beds 12, a single graphical room station communicates with both beds 12 through respective bed connectors. In such embodiments, screen 132 has a bed selector field 170 with a slider icon 172 therein which can be touched and dragged to the left and to the right within the field 170 to select whether screen 132 (and screen 134) display information relating to a first bed 12 (aka the "A" bed 12) or a second bed 12 (aka the "B" bed 12) in the semi-private room. In the illustrative example of screens 132, 134, the B bed 12 is selected because the slider icon 172 is located in the right side of field 170. Sliding the slider icon 172 to the left within field 170 results in deselection of the B bed 12 and selection of the A bed 12. Thus, a single graphical audio station can be used for selecting, enabling, and disabling the safety protocols of two beds 12 within the same room.

In some embodiments, slider icon 152 of field 148 and slider icon 172 of field 170 toggle to the left and to the right, successively, in response to a tap to the respective field 148, 170. In such embodiments, therefore, the user does not need to drag the icon 152, 172 to the new position, it will simply move to the new position in response to the single tap of the respective field 148, 170. However, all manners of making selections on graphical display screens are intended to be within the scope of this disclosure.

Still referring to embodiments of system 10 having a nurse call system compatible with bed 12, screens 132, 134 of the graphical audio station include a Menu icon 176, an Emergency icon 178, an Assist icon 180, and a Cancel icon 182. Menu icon 176 is selected by the user to navigate to a main menu screen. An example of a suitable menu screen is shown and described in U.S. Patent Application Publication No. 2011/0208541 A1 ("the '541 publication") which is hereby expressly incorporated by reference herein to the extent not inconsistent with the present disclosure which shall control as to any inconsistencies. See particularly, the discussion associated with FIG. 13 of the '541 publication.

Emergency icon 178 is selected in emergency situations to send simultaneously a call message to a designated response team of people. Thus, nurse call system 23 according to this disclosure is configured to send messages to wireless communication devices (pagers, smart phones, tablet computers, etc.) carried by caregivers. Assist icon 180 is also selected to send simultaneously a call message to a designated response team of people. The response teams are set up at the discretion of administrators of system 10 within healthcare facilities. It is typically the case that the response team associated with Assist icon 180 is smaller in number than the response team associated with Emergency icon 178. An alert level of the calls initiated by icons 178, 180 are different in some embodiments. For example, an emergency call initiated with button 178 may be at the highest alert level (e.g., red) whereas an assist call initiated with button 180 may be at an intermediate or low alert level (e.g., yellow).

In some embodiments, selection of each of icons 178, 180 results in a dome light of the associated patient room being illuminated to indicate either an emergency condition (e.g., red light on dome light) or assist condition (e.g., yellow light on dome light). Details of suitable dome light assemblies can be found in U.S. Pat. No. 8,384,526 which is already incorporated by reference. Cancel icon 182 is selected to cancel any of the calls made using either of icons 178, 180. In embodiments in which bed 12 communicates with a compatible nurse call system, any safety protocol violations, when enabled, are also communicated by control circuitry 110 of bed 12 to the nurse call system so that one or more lights of the dome light of the respective room is lit and so that messages of the protocol violation are sent to the wireless communication devices of one or more assigned caregivers. The messages concerning protocol violation include relevant information such as the room number in which the violation has occurred and the safety protocol (e.g., falls, pulmonary, and/or skin) and/or specific condition of the safety protocol (e.g., PPM alarming, brakes not set, HOB too low, etc.) that is violated.

Information concerning safety protocol status, including any protocol violations, may also be displayed on a status board of the nurse call system 23 in those embodiments in which bed 12 communicates with the nurse call system 23. Details of a suitable status board are shown and described in U.S. Pat. No. 8,779,924 which is hereby expressly incorporated by reference herein to the extent not inconsistent with the present disclosure which shall control as to any inconsistencies.

Illustrative screens 132, 134 also include a pair of status summary icons including a call bell icon 184 and a system alert icon 186. Each of icons 184, 186 have a number icon 188 that indicates the number of active calls or system alerts that are occurring unit wide as monitored by the nurse call system 23. In the illustrative example, there are two pending nurse calls as indicated by icon 188 adjacent call bell icon 184 and there is one system alert as indicated by icon 188 adjacent system alert icon 186. Selection of either of icons 184, 186 brings up associated information about the calls or alerts on the graphical room station. If there are no active calls or system alerts, then icons 184, 186 and the associated number icons 188 are not displayed on the graphical room station.

In some embodiments, some or all of the functions described above as being carried by control circuitry 110 of bed 12 in connection with the safety alert protocols are, instead, carried out at one or more remote servers such as a nurse call server and/or servers 20, 22, 24 and then communicated to control circuitry 110 of bed 12. Regardless of such remote decision making or support by remote servers and regardless of any safety alert protocols being selected and enabled automatically by a remote server, caregivers are able to manually override such decision making and automatic set up using screens 132, 134 of GUI 120 of bed 12 or of the graphical room station, as the case may be. Any such over rides made by a caregiver, such as deselecting any of the falls, pulmonary, or skin protocols using buttons 138, 140, 142, are communicated by control circuitry 110 back to the one or more remote servers, such as one or more of servers 20, 22, 24, that are in communication with bed 12.

Based on the foregoing, it can be seen that system 10 permits patient risk to be assigned based on patient information in the patient's EMR. Such patient risk assignment can be done by EMR server 22 or by another server or control circuitry 110 of bed 12 that pulls or receives the patient information from EMR server 22. Safety settings on bed 12 are then activated (e.g., enabled) based on patient presence, as determined by PPM system 70, and patient risk. Alerts are generated when the bed 12 is in a state that violates an enabled safety protocol condition for a patient of a given risk type. The alerts or alarms are automatically canceled or suppressed based on caregiver presence in the room as detected by RTLS 25 and communicated to bed 12. The alarms or alerts are automatically reset when the caregiver leaves the room as detected by the RTLS 25 is the alert conditions have not been rectified.

Screens 132, 134 give caregivers the ability to see the assigned risks (e.g., selected protocols) for the patients on beds 12 and the ability to suspend any alerts related to the safety protocols. Caregivers can also suspend the alerts based on a time in some circumstances and in some embodiments. Screens 132, 134 also permit caregivers to see patient detection status via the patient image of icon 166. In some embodiments, beds 12 have alert lights 126, 128, 130 to provide information regarding the status of the available safety protocols.

Although certain illustrative embodiments have been described in detail above, variations and modifications exist within the scope and spirit of this disclosure as described and as defined in the following claims.

The invention claimed is:

1. A patient bed for use in a healthcare facility having a network including a real time locating system (RTLS) and an electronic medical records (EMR) computer, the patient bed comprising
    a frame,
    a graphical user interface (GUI) coupled to the frame, and bed control circuitry coupled to the frame and to the GUI,
        the bed control circuitry being configured to receive at least one protocol message from the EMR computer and, in response to the at least one protocol message, enable at least one bed safety protocol in which at least one bed condition is monitored by the bed control circuitry, wherein the bed control circuitry generates an alert in response to the at least one bed condition being in an undesirable state and no caregiver being present in the patient room as determined by the RTLS and communicated to the bed control circuitry, wherein the bed control circuitry suspends monitoring the at least one bed condition in response to the RTLS indicating to the bed control circuitry that at least one caregiver is present in the patient room, wherein after the safety protocol has been suspended, the at least one bed safety protocol is re-enabled by the bed control circuitry in response to the RTLS indicating to the bed control circuitry that the at least one caregiver has left the patient room.

2. The patient bed of claim 1, wherein the GUI displays a screen having an icon that indicates whether the at least one bed safety protocol is enabled.

3. The patient bed of claim 2, wherein the GUI displays an icon that is used to manually disable further monitoring of the at least one bed condition of the at least on bed safety protocol.

4. The patient bed of claim 1, wherein the at least one bed safety protocol comprises a falls risk protocol which, when enabled, requires that a patient position monitoring system is monitoring patient position on the frame, requires that an upper frame portion of the frame is in a lowest position relative to a base portion of the frame, requires that one or more bed siderails of the frame are in a raised position, and requires that caster brakes of casters coupled to the frame are set.

5. The patient bed of claim 1, wherein the at least one bed safety protocol comprises a pulmonary protocol which, when enabled, requires a head section of a mattress support deck of the frame to be elevated above a threshold angle.

6. The patient bed of claim 5, wherein the threshold angle comprises about 30 degrees.

7. The patient bed of claim 1, wherein the at least one bed safety protocol comprises a skin protocol which, when enabled, requires the patient to move on the frame by a threshold amount so as not to be stationary for a threshold amount of time.

8. The patient bed of claim 1, wherein the at least one bed safety protocol comprises at least three bed safety protocols and further comprising three alert lights coupled to the frame, each alert light of the three alert lights corresponds to a respective one of the three bed safety protocols.

9. The patient bed of claim 8, wherein each alert light of the three alert lights is illuminated a first color when the respective bed safety protocol is enabled and the at least one bed condition of the respective bed safety protocol is in a desirable state and wherein each alert light of the three alert lights is illuminated a second color when the respective bed safety protocol is enabled and the at least one bed condition of the respective bed safety protocol is in an undesirable state.

10. The bed alert system of claim 9, wherein each alert light of the three alert lights is turned off when the respective bed safety protocol is disabled.

11. The patient bed of claim 8, wherein the frame extends between a head end and a foot end and the three alert lights are coupled to the foot end of the frame.

12. The patient bed of claim 1, wherein the at least one bed safety protocol in which at least one bed condition is monitored by the bed control circuitry is enabled only if a patient position monitoring system coupled to the frame senses that a patient is present on the patient bed.

13. The patient bed of claim 1, wherein the bed control circuitry suspends monitoring the at least one bed condition for a threshold period of time such that, after the threshold period of time, the at least one bed safety protocol is re-enabled by the bed control circuitry.

14. The patient bed of claim 13, wherein the GUI displays an input that is used to command the bed control circuitry to extend the threshold period of time.

15. The patient bed of claim 13, wherein after the safety protocol has been suspended, the at least one bed safety protocol is re-enabled by the bed control circuitry in response to the RTLS indicating to the bed control circuitry that the at least one caregiver has left the patient room even if the threshold period of time has not yet been reached.

16. The patient bed of claim 1, wherein the bed control circuitry communicates with the RTLS and the EMR computer via a wired connection from the bed to a connector located in the patient room.

17. The patient bed of claim 1, wherein the bed control circuitry communicates with the RTLS and the EMR computer via wireless transmissions within the patient room.

18. A bed alert system comprising the patient bed of claim 1 and a bed connector at a fixed location in a patient room in which the patient bed is located, the bed connector being in communication with the bed control circuitry, the bed connector operating as a communication link through which messages are sent from the patient bed to the network and through which messages are received by the bed from the network, wherein the bed control circuitry is configured to receive the at least one protocol message from the EMR computer via the bed connector.

19. The bed alert system of claim 18, wherein the bed control circuitry suspends monitoring the at least one bed condition for a threshold period of time such that, after the threshold period of time, the at least one bed safety protocol is re-enabled by the bed control circuitry and wherein after the safety protocol has been suspended, the at least one bed safety protocol is re-enabled by the bed control circuitry in response to the RTLS indicating to the control circuitry of the patient bed via the bed connector that the at least one caregiver has left the patient room even if the threshold period of time has not yet been reached.

20. A patient bed for use in a healthcare facility having a network including a real time locating system (RTLS) and an electronic medical records (EMR) computer, the patient bed comprising
    a frame,
    a graphical user interface (GUI) coupled to the frame, and
    bed control circuitry coupled to the frame and to the GUI, the bed control circuitry being configured to receive at least one protocol message from the EMR computer and, in response to the at least one protocol message, enable at least one bed safety protocol in which at least one bed condition is monitored by the bed control circuitry, wherein the bed control circuitry generates an alert in response to the at least one bed condition being in an undesirable state and no caregiver being present in the patient room as determined by the RTLS and communicated to the bed control circuitry, wherein the bed control circuitry suspends monitoring the at least one bed condition in response to the RTLS indicating to the bed control circuitry that at least one caregiver is present in the patient room, wherein the at least one bed safety protocol comprises a falls risk protocol which, when enabled, requires that a patient position monitoring system is monitoring patient position on the frame, requires that an upper frame portion of the frame is in a lowest position relative to a base portion of the frame, requires that one or more bed siderails of the frame are in a raised position, and requires that caster brakes of casters coupled to the frame are set.

21. A patient bed for use in a healthcare facility having a network including a real time locating system (RTLS) and an electronic medical records (EMR) computer, the patient bed comprising
    a frame,
    a graphical user interface (GUI) coupled to the frame, and
    bed control circuitry coupled to the frame and to the GUI, the bed control circuitry being configured to receive at least one protocol message from the EMR computer and, in response to the at least one protocol message, enable at least one bed safety protocol in which at least one bed condition is monitored by the bed control circuitry, wherein the bed control circuitry generates an alert in response to the at least one bed condition being in an undesirable state and no caregiver being present in the patient room as determined by the RTLS and communicated to the bed control circuitry, wherein the bed control circuitry suspends monitoring the at least one bed condition in response to the RTLS indicating to the bed control circuitry that at least one caregiver is present in the patient room, wherein the bed control circuitry suspends monitoring the at least one bed condition for a threshold period of time such that, after the threshold period of time, the at least one bed safety protocol is re-enabled by the bed control circuitry, wherein after the safety protocol has been suspended, the at least one bed safety protocol is re-enabled by the bed control circuitry in response to the RTLS indicating to the bed control circuitry that the at least one caregiver has left the patient room even if the threshold period of time has not yet been reached.

22. A bed alert system for use in a healthcare facility having a network including a real time locating system (RTLS) and an electronic medical records (EMR) computer, the bed alert system comprising
    a patient bed comprising a frame, a graphical user interface (GUI) coupled to the frame, and bed control circuitry coupled to the frame and to the GUI, the bed control circuitry being configured to receive at least one protocol message from the EMR computer and, in response to the at least one protocol message, enable at least one bed safety protocol in which at least one bed condition is monitored by the bed control circuitry, wherein the bed control circuitry generates an alert in response to the at least one bed condition being in an undesirable state and no caregiver being present in the patient room as determined by the RTLS and communicated to the bed control circuitry, wherein the bed control circuitry suspends monitoring the at least one bed condition in response to the RTLS indicating to the bed control circuitry that at least one caregiver is present in the patient room, and a bed connector at a fixed location in a patient room in which the patient bed is located, the bed connector being in communication with the bed control circuitry, the bed connector operating as a communication link through which messages are sent from the patient bed to the network and through which messages are received by the bed from the network, wherein the bed control circuitry is configured to receive the at least one protocol message from the EMR computer via the bed connector, wherein the bed control circuitry suspends monitoring the at least one bed condition for a threshold period of time such that, after the threshold period of time, the at least one bed safety protocol is re-enabled by the bed control circuitry and wherein after the safety protocol has been suspended, the at least one bed safety protocol is re-enabled by the bed control circuitry in response to the RTLS indicating to the control circuitry of the patient bed via the bed connector that the at least one caregiver has left the patient room even if the threshold period of time has not yet been reached.

* * * * *